United States Patent [19]

Lundquist

[11] 4,332,254
[45] Jun. 1, 1982

[54] SYSTEM FOR FILLING AND INFLATING AND DEFLATING A VASCULAR DILATING CATHETHER ASSEMBLY

[75] Inventor: Ingemar Lundquist, Oakland, Calif.

[73] Assignee: Advanced Catheter Systems, Inc., Palo Alto, Calif.

[21] Appl. No.: 207,732

[22] Filed: Nov. 17, 1980

[51] Int. Cl.$^3$ ................ A61M 29/02; A61M 25/00
[52] U.S. Cl. ........................... 128/344; 60/579; 92/98 R; 128/349 B
[58] Field of Search ............ 128/344, 349 B, 348, 128/246; 60/579; 92/97, 98 R

[56] References Cited

U.S. PATENT DOCUMENTS

| | | | |
|---|---|---|---|
| 2,667,184 | 1/1954 | Hailer et al. | 92/98 R |
| 3,064,429 | 11/1962 | Hager | 60/579 |
| 3,769,960 | 11/1973 | Robinson | 92/98 R |
| 4,195,637 | 4/1980 | Grüntzig et al. | 128/349 B |

Primary Examiner—Stephen C. Pellegrino
Attorney, Agent, or Firm—Flehr, Hohbach, Test, Albritton & Herbert

[57] ABSTRACT

A system for filling and subsequently producing inflation and deflation of a balloon-type dilating catheter assembly utilized in performing a percutaneous transluminal coronary angioplasty procedure. Separate primary and secondary fluid pump assemblies are provided for isolating the working pump fluid in the primary assembly from the radiocontrast medium filling the secondary assembly. The primary fluid pump assembly includes a primary pump chamber having a flexible diaphragm forming one wall thereof and a hydraulic cylinder including a piston for supplying fluid under pressure to the pump chamber. The pump assembly has been filled with a relatively incompressible liquid while the piston in the cylinder is held in an intermediate fill position and the diaphragm is held substantially flat to enable the primary fluid pump assembly to produce both convex and concave shapes of the diaphragm as the piston is moved between forward and rearward position. The second fluid pump assembly is adapted to mount to the primary pump chamber. The secondary fluid pump assembly includes a secondary pump chamber having a second flexible diaphragm forming one wall thereof and adapted to mate with the first flexible diaphragm. A resealing fluid entry port is provided in the secondary pump chamber for admitting fluid to the chamber. A bayonet mounting arrangement for mounting the secondary pump chamber to the primary pump chamber is provided to bring the two diaphragms into intimate physical contact. Manual and automatic means for driving the piston of the hydraulic cylinder between forward and backward positions are disclosed to alternately create both balloon-inflating pressure and balloon-deflating vacuum in the secondary pump chamber and dilating catheter assembly by way of the diaphragms after it is filled with a relatively incompressible fluid.

21 Claims, 11 Drawing Figures

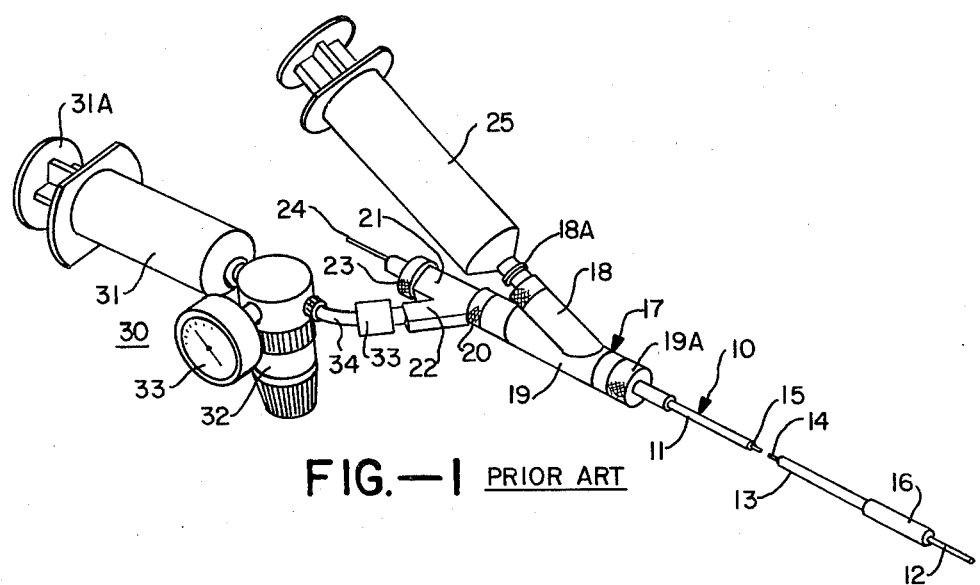
FIG.—1 PRIOR ART
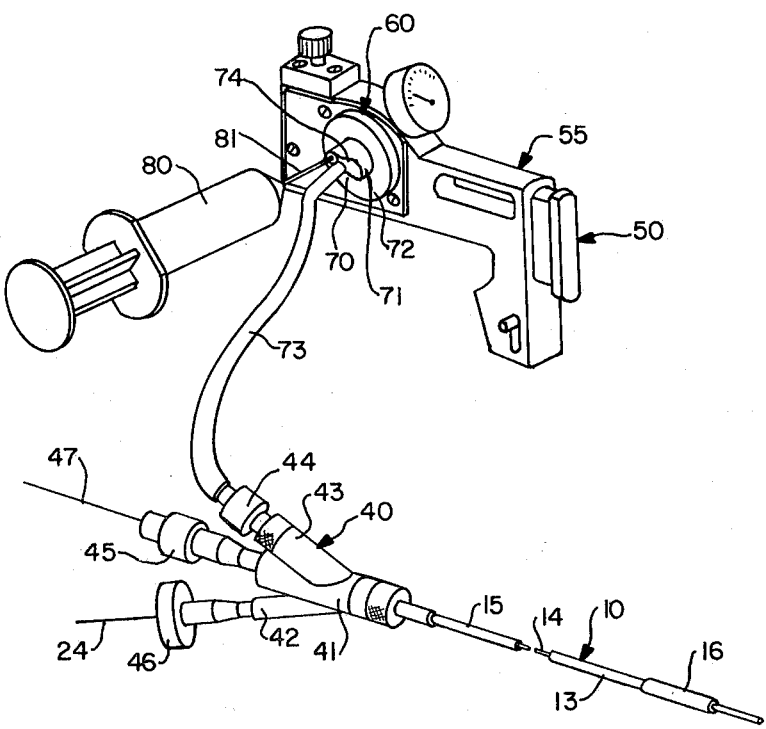
FIG.—2

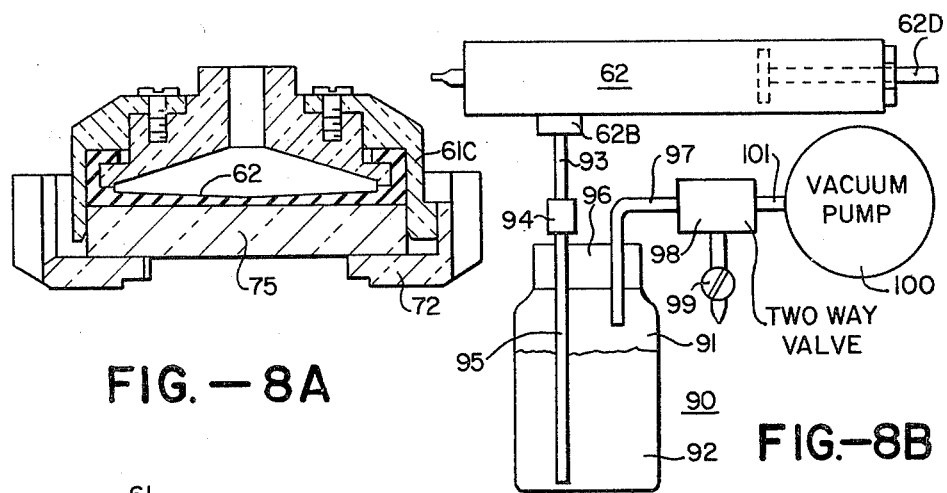
FIG.—8A
FIG.-8B
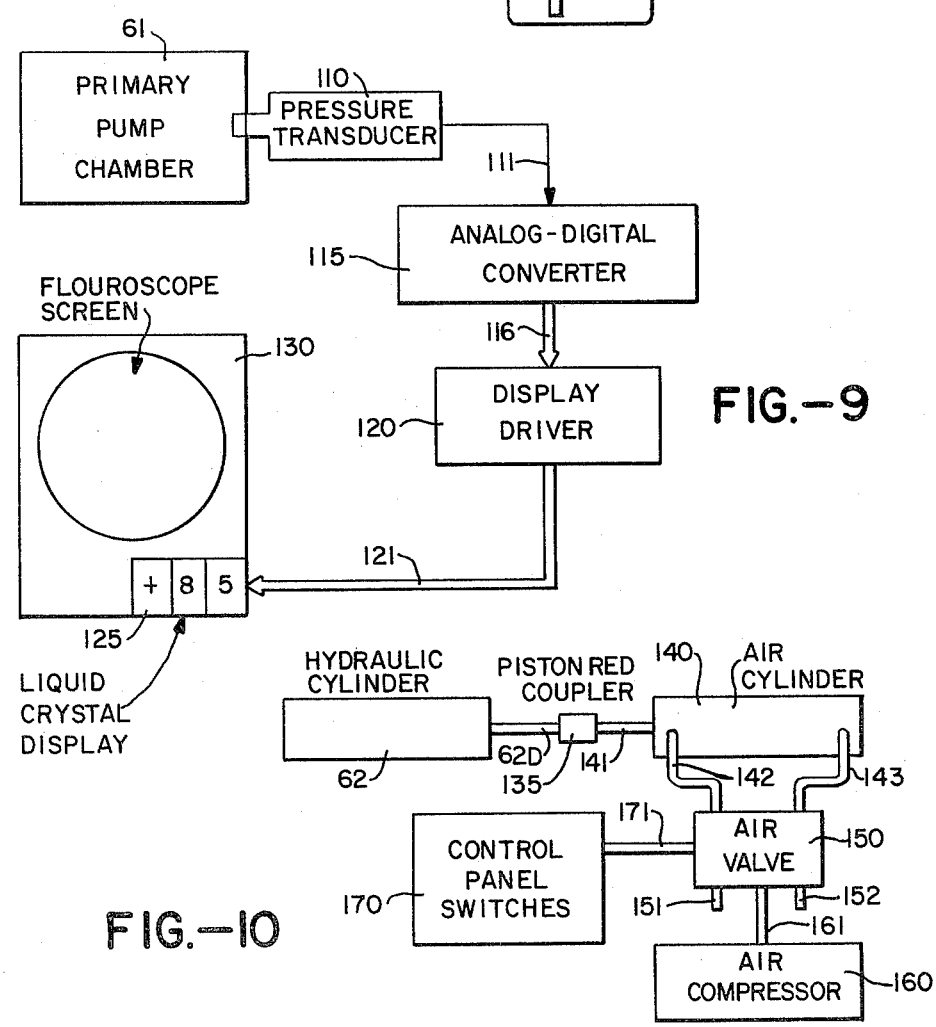
FIG.-9
FIG.-10

SYSTEM FOR FILLING AND INFLATING AND DEFLATING A VASCULAR DILATING CATHETHER ASSEMBLY

This invention relates generally to a surgical technique called percutaneous transluminal coronary angioplasty utilizing a vascular dilating catheter assembly. More specifically this invention relates to a system for filling the vascular dilating catheter assembly and for inflating and deflating a balloon portion of the catheter near the distal end thereof.

Several years ago a new procedure was developed by A. Grüntzig for reducing atherosclerotic lesions in coronary arteries which is called percutaneous transluminal coronary angioplasty.

The Grüntzig et al. technique involves use of a catheter system introduced via the femoral artery under local anesthesia. A preshaped guiding catheter is positioned in the orifice of the coronary artery and through this catheter a second dilation catheter is advanced into the branches of the coronary artery. The dilating catheter has an elliptical-shaped distensible balloon portion formed near the distal tip of the catheter which can be inflated and deflated. After traversing the stenotic lesion of the coronary artery, the distensible balloon portion is inflated with fluid under substantial pressure which compresses the atherosclerotic material in a direction generally perpendicular to the wall of the vessel, thereby dilating the lumen of the vessel.

Catheter assemolies useful in performing percutaneous transluminal coronary angioplasty are disclosed in the copending Simpson et al. U.S. patent application entitled "Vascular Guiding Catheter Assembly and Vascular Dilating Catheter Assembly and a Combination Thereof and Methods for Making the Same", Application Ser. No. 151,175, filed May 19, 1980, and assigned to the assignee of this invention. The disclosure of this application is specifically incorporated herein by reference for its discussion of the structural details of a guiding catheter assembly and dilating catheter assembly useful in conjunction with this invention together with the surgical method involved in utilizing the catheter system.

Some troublesome aspects of performing percutaneous transluminal coronary angioplasty have involved the system for initially filling the dilating catheter assembly with radiocontrast fluid before the dilating catheter is inserted into the patient, keeping the balloon section deflated while the catheter is inserted in the patient and also providing good pressure inflation and vacuum deflation action of the balloon portion after the catheter is in place. The prior art system for performing these operations is generally discussed in the above-referenced Simpson et al. patent application and utilizes components of the type shown in FIG. 1 of the attached drawings.

As shown in FIG. 1, the dilating catheter assembly 10 includes a coaxial tube catheter section 13 which is adapted to be inserted into the patient and a connector structure 17 which enables both the inner and outer channels of the coaxial catheter to be supplied with radiocontrast fluid. As shown the catheter assembly 10 has an inner tube 14 and an outer tube 15 which extend the length of the catheter. At the proximal end 12 of the outer tube 15 a distensible thin wall balloon section 16 has been formed. At the proximal end 11 of the catheter assembly the coaxial tubes 14 and 15 are fed into the connector assembly 17. The inner tube 14 is fed into a side arm 18 where it is sealed into a fitting 18A. The fitting 18A is adapted to receive the front end of syringe 25 in order to supply radiocontrast media through the central tube into the artery when it is desired to determine the position of the catheter or the progress of the catheter in reaching the constricted area of the vessel. A connecting arrangement 19A connects the outer tube 15 into the main central arm of connector 17 which is connected through a coupler 20 to a branching connector 21 which has a central portion and a side arm 22. A valve arrangement 23 is provided on the rear end of the central section 21 to permit a flush wire 24 to be inserted through the channel between the inner catheter tube 14 and the outer catheter tube 15 into the balloon section 16 to provide a passageway for air to be flushed out of the balloon section 16 while the outer channel of the catheter and the balloon are being filled with radiocontrast liquid.

The side arm 22 is coupled via a connector 33 and tubing 34 to a pumping arrangement 30 which is utilized to initially fill the outer channel and balloon 16 of catheter 10 with the radiocontrast fluid. The pumping arrangement 30 includes a syringe pump 31 filled with radiocontrast fluid, a pressure regulating valve 32 connected between syringe 31 and the fill tubing 34 to set the maximum balloon inflation pressure, and a dial pressure gage 33 to enable reading of the fluid pressure applied to the catheter by the syringe pump 31.

Prior to inserting the catheter 10 in the patient, the outer channel of the catheter 10 and the balloon 16 are filled by using syringe 31 to deliver radiocontrast fluid into these areas of the catheter until the areas are completely filled and all air has escaped through the flush wire 24. Thereafter flush wire 24 is removed and the valve arrangement 23 through which it extends is closed. The balloon section 16 of catheter 10 is then deflated by pulling back on the handle 31A of syringe pump 31. It is important to keep the balloon section 16 collapsed while inserting the dilating catheter 10 through the guiding catheter assembly (not shown) to make it easy for the dilating catheter to traverse the guiding catheter and to enter the section of the coronary artery which is to be treated. It will thus be seen that, in this prior art system, one person is required for holding the syringe pump and maintaining a partial vacuum on the fluid to keep the balloon collapsed while another person is inserting the catheter into the patient.

In addition to the difficulty involved in coordinating the two person effort to insert the catheter into the patient, the system shown in FIG. 1 creates other problems for the medical team. Since the radiocontrast medium supplied to the dilating catheter is supplied through the pressure regulator valve 32, each time the operation is performed the pressure regulator valve and the dial pressure gage 33 have to be sterilized. The combination of the sterilization operation and the corrosive effect of the radio contrast medium which is pumped through the pressure regulator valve tend to corrode the components. Consequently, these components require frequent cleaning, thereby creating unwelcome maintenance problems in the operating room.

Accordingly, it is an object of this invention to provide an improved system for initially filling a dilating catheter with radiocontrast fluid and thereafter inflating and deflating the balloon portion of the catheter.

It is another object of this invention to provide a system for initially filling and later inflating and deflating the balloon portion of a dilating catheter assembly in which the secondary pump assembly communicating radiocontrast fluid to the dilating catheter is separate from the primary pump assembly which generates pressure and vacuum for inflation and deflation of the balloon portion.

It is another object of this invention to provide a system of the aforementioned type in which the secondary pump assembly is sterilizable and disposable.

It is another object of this invention to provide a system of the aforementioned type in which the primary fluid pump assembly automatically maintains a vacuum in the secondary fluid pump assembly to keep the balloon section of the catheter collapsed while inserting it in the patient.

The above-stated objects are attained in accordance with one aspect of this invention in an apparatus for rapid inflation and deflation of a balloon-type dilating catheter assembly which utilizes a pistol grip housing adapted to be held in one hand and having spring loaded actuator means mounted thereon and adapted to be operated by a portion of said hand holding said housing between a released, balloon deflation position and an actuated, balloon inflation position. A pump means is at least partly carried by the housing and is coupled to the actuator means to be actuated thereby. The pump means includes a pump chamber adapted to be connected to the catheter assembly and piston means coupled to the actuator means for altering the fluid holding volume of the pump chamber, latching means is provided on the housing for holding the actuating means in a catheter fill position intermediate the released, balloon deflation position and an extreme actuated, balloon inflation position. A fill port means is carried on the pump chamber for filling the pump chamber and the catheter assembly with a relatively incompressible fluid when the actuator is latched in the catheter fill position. In this manner a balloon deflation vacuum is automatically produced in the pump chamber when the actuator is in the released position and a balloon inflation pressure is produced in the pump chamber when the actuator is moved to an inflation position.

Preferably, the pump chamber is a secondary pump chamber and the pump means further includes a primary pump chamber and a flexible diaphragm mounted between the primary and secondary pump chambers. The piston means is carried in the primary pump chamber and the flexible diaphragm forms a portion of one wall of the primary pump chamber to provide a completely sealed chamber. The secondary pump chamber is adapted to mount to the primary pump chamber over the flexible diaphragm in a sealed relation. The primary pump chamber is filled with a relatively incompressible fluid while the diaphragm means is held in a substantially flat position and the actuator means is held in a factory fill position intermediate the catheter fill position and the released position. This enables the piston in the primary pump chamber to operate the flexible diaphragm to create balloon deflating vacuum in the released position of the actuator means and balloon inflating pressure in the actuated position of the actuating means.

The above-stated objects are attained in accordance with another aspect of this invention in an apparatus for rapid inflation and deflation of a balloon-type dilating catheter assembly which utilizes a primary fluid pump assembly comprising a primary pump chamber having a first flexible diaphragm forming one wall thereof and a hydraulic cylinder including a piston for supplying fluid under pressure to the pump chamber. The pump assembly is filled with a relatively incompressible liquid while the piston is held in an intermediate fill position and the diaphragm is held substantially flat to produce both concave and convex shapes of the diaphragm as the piston is thereafter moved between forward and rearward positions. A secondary fluid pump assembly adapted to mount to the primary pump chamber is provided and comprises a secondary pump chamber adapted to mate with the first flexible diaphragm in a fluid-tight relation.

Preferably, the secondary fluid pump assembly has a second flexible diaphragm forming one wall thereof and being adapted to mate with the first flexible diaphragm. The secondary pump chamber also includes a resealing fluid entry port means for admitting fluid to the secondary chamber and means for mounting the secondary pump chamber to the primary pump chamber with the first and second diaphragms in intimate physical contact. The secondary fluid pump assembly also includes means for communicating fluid between the secondary pump chamber and the dilating catheter assembly. Finally means are provided for driving the piston of the hydraulic cylinder between the forward and backward positions thereby to alternately create balloon inflating pressure and balloon deflating vacuum in the secondary pump chamber and the dilating catheter assembly after they are filled with a relatively incompressible fluid.

Preferably, the primary fluid pump assembly is mounted in a portable housing which includes a pistol grip handle on one hand with the piston rod of the hydraulic cylinder extending into the handle. In this preferred embodiment the driving means comprises a pump actuator fastened to the piston rod and means for mounting the actuator on the handle for enabling the actuator to drive the piston rod in response to manual operation by a hand holding the handle. Preferably a spring biasing means is provided for biasing the actuator and the attached piston toward the rearward position for automatically maintaining a vacuum in the secondary pump chamber and the dilating catheter assembly to keep the balloon deflated while inserting the dilating catheter into the patient.

Preferably, the secondary pump chamber comprises a molded plastic housing having a generally hollow, cylindrical configuration with one end of the housing being open and having a rim portion formed thereon and the other end of the housing having a cap portion formed thereon with the fluid channel extending through it. The cap portion is fastened to a length of flexible plastic tubing to communicate fluid from the interior of the plastic housing to the catheter assembly. The second flexible diaphragm preferably has a generally cup-shaped configuration and is adapted to snap over the rim portion on the housing to form therewith a generally fluid-tight seal.

In this preferred embodiment the resealing fluid entry port comprises a well formed in one wall of the plastic housing between the cap portion and the rim and the well is adapted to receive the end of a syringe needle. A resealing rubber membrane is fitted over the mouth of the well and is adapted to be pierced by the syringe needle. A cap is fastened to the housing over the rubber membrane to keep it in place and has an aperture in the top thereof which is adapted to admit the syringe needle into the well through the membrane. An interior wall of the well is provided with a fill opening formed in a section thereof opposite the tip of the needle when fully inserted to communicate fluid from the well to the interior of the housing.

In a preferred embodiment the structure of the primary pump chamber is adapted for a quick connect-disconnect type mounting of the secondary pump chamber thereon. A mounting cup in the primary pump chamber which partially receives the diaphragm of the secondary pump chamber cooperates with a mounting cap adapted to fit over the secondary pump chamber, with the mounting cup of the primary pump chamber and the mounting cap having cooperative structures providing a bayonet screw type mounting arrangement which urges the end wall of the second diaphragm into contact with the end wall of the first diaphragm within the mounting cup.

The system of this invention provides several important advantages over the prior art system of filling and inflating and deflating the balloon portion of the dilating catheter assembly. A principal advantage is that the primary pump assembly is physically separate from the secondary pump assembly so that the primary pump assembly is not subject to the corrosive effects of the radiocontrast fluid or to sterilizing operations repeatedly performed thereon. Instead, the primary pump assembly is a separate sealed unit which can be sterilized and then maintained in a sterile condition within the operating room environment. Because the primary pump assembly includes an actuator arrangement which is spring biased to a position which maintains vacuum in the secondary pump chamber and the dilating catheter assembly, catheter insertion can be a one person operation. In addition, the use of a disposable secondary fluid pump assembly with a convenient resealing fluid entry port together with providing a latched catheter fill position for the actuator means associated with the primary fluid pump assembly makes the filling of the catheter prior to insertion into the patient a very simple operation. The primary fluid pump assembly and associated driving means can readily be mounted in a plastic housing with a pistol grip arrangement which makes it very easy for the operating room personnel to rapidly inflate and deflate the balloon portion of the catheter after insertion into the patient. In a preferred embodiment, the disposable secondary fluid pump assembly is a fluid-tight assembly which eliminates any mess in disassembling it from the primary fluid pump assembly.

Other objects, features, and advantages of this invention will be apparent from a consideration of the following detailed description in conjunction with the accompanying drawings.

FIG. 1 is an isometric view of a prior art system for filling, inflating, and deflating of a dilating catheter assembly.

FIG. 2 is an isometric view of components of one embodiment of a system for filling, inflating, and deflating a dilating catheter assembly in accordance with this invention.

FIG. 8A is a section view through a portion of the apparatus of this invention useful in explaining the filling procedure of the inflation-deflation gun.

FIG. 8B is a schematic diagram useful in explaining the initial fill operation on an inflation-deflation gun assembly in accordance with this invention.

FIG. 9 is a schematic diagram of an alternate pressure readout approach useful in conjunction with the system of this invention.

FIG. 10 is a schematic diagram of an alternate driving means for the system of this invention.

Figure 3:
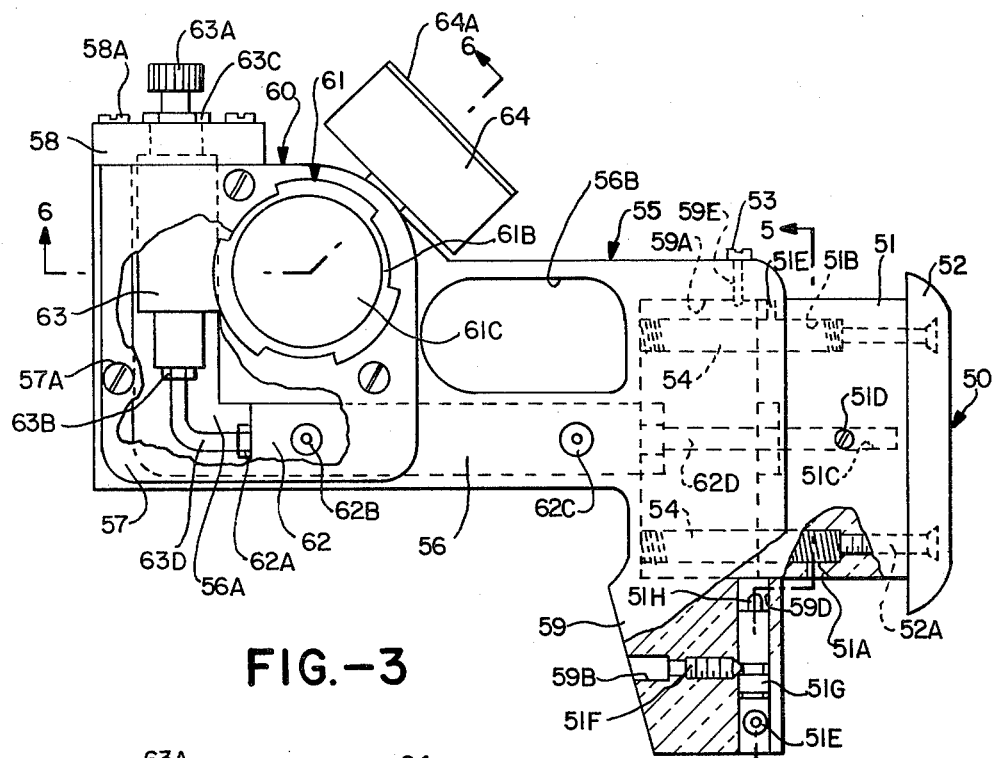
FIG. 3 is an elevational view of a catheter inflation-deflation gun assembly in accordance with this invention.

Referring now to the drawings, FIG. 2 shows the overall arrangement of a preferred system for filling, inflating, and deflating a dilating catheter in accordance with this invention. For shorthand purposes, this system hereafter will be referred to as a dilating catheter inflation system or catheter inflation system, but it should be understood that this reference is simply a shorthand reference and is not intended to limit the function of the invention. The catheter inflation system depicted in FIG. 2 is intended for use with the same type of dilating catheter assembly as is depicted in FIG. 1. However, the connector portion 40 of the dilating catheter assembly 5 shown in FIG. 2 is improved over the connector assembly 17 shown in FIG. 1.

The coaxial dilating catheter portion 10 is identical to the catheter depicted in FIG. 1 and need not be described in detail in conjunction with FIG. 2. The connector assembly 40 for the dilating catheter utilizes a triple-Y type of chamber structure with a central body portion 41 and a pair of side arms 42 and 43. The central body portion 41 and the side arms 42 and 43 each have a hollow interior which communicates with the port at the back end of the connector. In this connector assembly, the central tube 14 extends through the central body portion 41 and is attached to a fitting assembly 45 which seals the interior of the inner tube 14 from any communication with the fluid channel between the inner tube 14 and the outer tube 15. Both of the side arms 42 and 43 thus communicate only with the outer annular channel between the inner and outer tubes 14 and 15 of the catheter assembly 10. Side arm 43 has a fitting arrangement 44 utilized to connect the end of the side arm to a section of plastic tubing 73 forming part of the catheter inflation system of this invention. Side arm 42 includes an O-ring valving arrangement 46 which is adapted to receive the flush wire 24 which extends through the annular channel between inner tube 14 and outer tube 15 into the balloon section 16 of the catheter.

The catheter inflation system of this invention includes a primary fluid pump assembly generally designated 60, a secondary fluid pump assembly 70 and an actuating means 50 for the primary fluid pump assembly 60. The primary fluid pump assembly 60 includes, in a preferred embodiment, a primary pump chamber, a pressure regulating valve, and a hydraulic cylinder all of which are partially or completely mounted within housing 55 and will be shown and described in detail in other drawings and description given below. The basic elements of the second fluid pump assembly 70 which is adapted to mount over the primary pump chamber of the primary fluid pump assembly comprise a secondary pump chamber 71, a resealing fluid entry port means 74, a mounting means 72 for mounting the secondary pump chamber 71 on the primary pump chamber, and a means 73 in the form of flexible tubing for communicating fluid between secondary pump chamber 71 and dilating catheter assembly 5. A syringe 80 having a needle 81 on one end thereof is shown in FIG. 2 with the end of needle 81 entering the resealing fluid entry port means 74 for introducing radiocontrast fluid into the secondary pump chamber 71 and through the tubing means 73 into catheter assembly 10. Details of the structure and operation of the various components of the catheter inflation system of this invention are shown in the other drawings and will be described in detail below. These details need to be understood before an overall description of the function of the catheter inflation system of this invention can be given.

Figure 4:
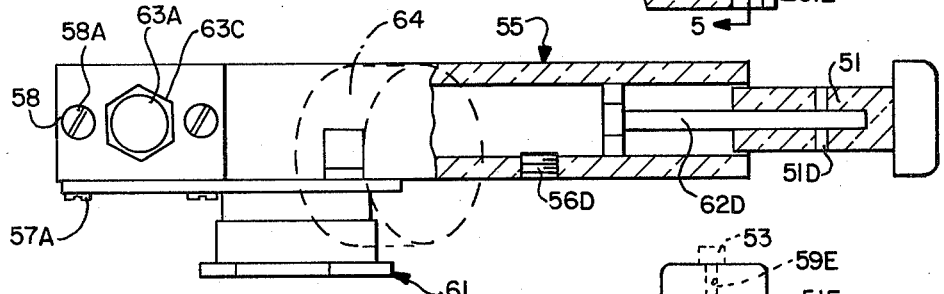
FIG. 4 is a partial top view of a catheter inflation-deflation gun assembly in accordance with this invention.
Figure 5:
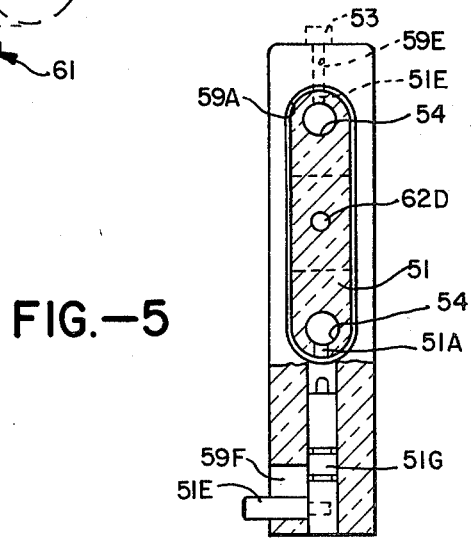
FIG. 5 is a partial section view of a catheter inflation-deflation gun of FIG. 3 taken along the lines 5—5.
Figure 6:
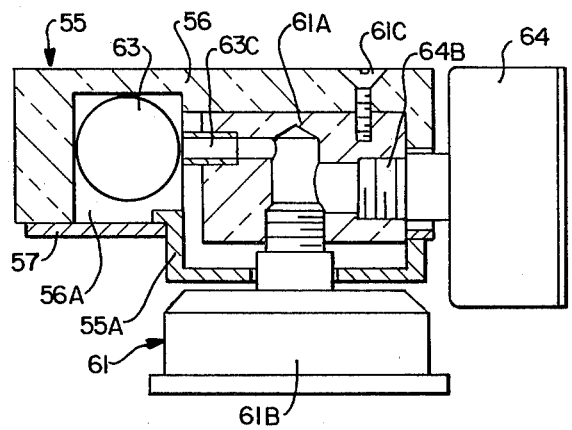
FIG. 6 is a partial section view of a portion of a catheter inflation-deflation gun in accordance with this invention taken along the lines 6—6 in FIG. 3.
Figure 7:
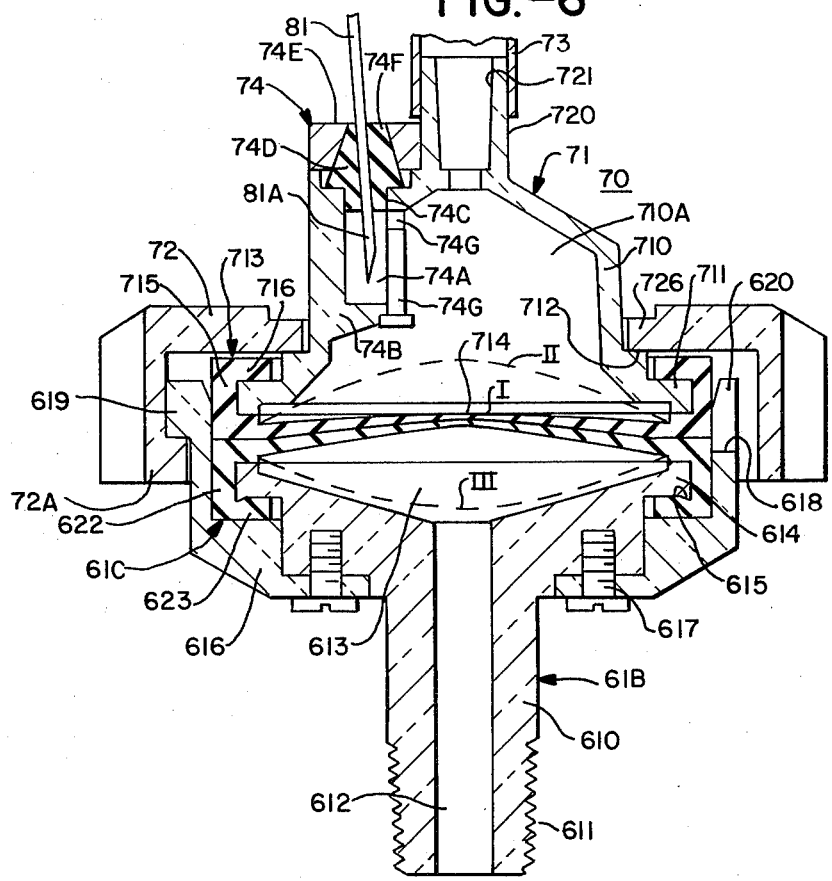
FIG. 7 is a section view of a portion of a system for filling, inflating, and deflating a dilating catheter assembly in accordance with this invention.

Referring now to FIGS. 3-6, the structural details of a preferred embodiment of a catheter inflation system designed for manual operation will be described. The primary fluid pump assembly 60 of this preferred embodiment includes a primary pump chamber 61, a hydraulic cylinder 62, a variable pressure regulating valve 63, and a compound pressure gage means 64. As shown particularly in FIG. 6, the primary pump chamber 61 includes a multiport block 61A and a diaphragm assembly 61B which threads into one of the ports of multiport block 61A. Hydraulic cylinder 62, pressure regulating valve 63 and multiport block 61A are all positioned within a machined-out cavity 56A in the main section 56 of housing 55. Hydraulic cylinder 62 is maintained in place within cavity 56A by the air vent valve arrangement 62C thereon which extends through an aperture 56D in main housing section 56. The fluid delivery port 62A of hydraulic cylinder 62 is coupled to pressure regulating valve 63 by means of a flexible tube 63D. A threaded coupler 63C which threads into multiport block 61A connects the exit port of pressure regulating valve 63 into the primary pump chamber 61. A thumb screw 63A on regulating valve 63 is used to set the pressure limit of the valve. Pressure regulating valve 63 is retained in position within cavity 56A by means of a nut 63C mounted on a threaded portion of the valve which extends through the cap 58A which is mounted to housing 55 by way of mounting screws 58A. The multiport block 61A is maintained in position within cavity 56A by means of one or more screws 61C shown in FIG. 6. Also shown in FIG. 6 is a plastic cap 55A which covers part of the cavity 56A behind the diaphragm assembly 61B. A metal cover plate 57 fits over the diaphragm assembly 61B and covers the remainder of the cavity 56A in housing 55. The structural details of the diaphragm assembly 61B are shown in FIG. 7 and will be discussed later.

Housing 55 includes a main body section 56 and a pistol grip handle section 59. An aperture 56B formed through the main body section 56 cooperates with pistol grip handle 59 to enable a person to grip the housing in a comfortable fashion using one or two fingers in the aperture 56B and the rest of the fingers on the handle section 59. Handle section 59 of housing 55 includes a channel 59A formed in the top rear portion thereof which is adapted to receive an actuating bar 51 in a sliding fashion. The piston rod 62D of hydraulic cylinder 62 extends through channel 59A and is received in a well 51C formed within actuator bar 51. A pair of set screws 51D are mounted in threaded apertures through the actuator bar 51 to retain actuator bar 51 in a fixed position on piston rod 62D. A palm fitting bar 52 is mounted to actuator bar 51 by means of a pair of screws 52A. Actuator bar 51 has a pair of wells 51B formed in the back wall thereof for receiving a pair of compression springs 54 which urge actuator bar 51 toward its maximum rearward position with the piston (not shown) within hydraulic cylinder 62 at its maximum backward position.

Handle section 59 includes an aperture 59E communicating between the top of housing 55 and the channel 59A. An aperture 51E is formed in the top of actuator bar 51 in a location which will bring it into registration with the aperture 59E when the actuator bar 51 is pushed into an intermediate position. When these two apertures 59E and 51E are aligned, a latch pin 53 may be inserted therein to retain actuator bar 51 and the piston in cylinder 62 in an intermediate position which is designated the "factory gun fill position".

Handle 59 also includes a threaded aperture 59B adapted to receive a detent mechanism 51F and an aperture 59D adapted to receive a latch bar 51G. As shown in FIGS. 3 and 5, the latch bar 51G has a pair of detent rings formed therein which cooperate with the detent assembly 51F to maintain latch bar 51G in one of two detent positions. In the lower detent position the latch bar head 51H is retracted below the actuator bar 51 and in the upper latch bar position the latch bar head 51H is adapted to enter the latch channel 51A formed in the bottom of actuator bar 51. With latch bar head 51H in channel 51A, actuator bar 51 is maintained in an intermediate position which is designated the "catheter fill position". The back wall of the channel 51A is sloped so that, when actuator bar 51 is pushed in, the latch bar head 51H will be forced out of channel 51A. Then when actuator bar 51 is released, it retracts under spring pressure to its maximum extension. The purpose of this will be discussed below. A latch bar handle 51E extends through aperture 59F in housing 55 to enable latch bar 51G to be manually moved between its upper and lower detent positions.

FIG. 7 illustrates the structural details of the diaphragm assembly 61B comprising a portion of the primary pump chamber 61 and the preferred form of a secondary fluid pump assembly 70 which is adapted to be mounted on diaphragm assembly 61B using a bayonet type mounting arrangement involving a cap 72. First, considering the structure of diaphragm assembly 61B, a housing 610 is provided with a threaded back portion 611 which enables it to be threaded into the multiport block 61A shown in FIG. 6. A channel 612 extends through the back stem of the housing 61B to communicate fluid to an open cylindrical working chamber 613. Housing 610 has a rim 614 formed thereon so that the cup-shaped diaphragm 61C may be snapped over it. Diaphragm 61C has a thin end wall portion 621 and a thicker side wall portion 622 with an interior lip 623 formed thereon. Lip 623 snaps behind rim 614 on housing 610. A mounting cup 616 receives housing 610 and diaphragm 61C with a pair of mounting screws 617 fastening housing 610 in mounting cup 616. A sealing projection 615 formed on rim 614 bites into the interior lip 623 on diaphragm 61C as housing 610 is drawn into mounting cup 616 by the screws 617. This forms a highly fluid tight chamber between the flaired interior portion 613 of housing 610 and the thin wall portion 621 of diaphragm 61C.

Secondary fluid pump assembly 70 comprises a molded plastic housing 71 which has generally cylindrical side walls 710 which form an interior fluid reservoir area 710A. The bottom end of housing 71 is open and the top end includes a cap portion 720 having a channel 721 extending therethrough. Below the cap portion 720, the side walls 710 are tapered to ensure that no pockets for trapping air will be formed as the reservoir area 710A is filled with fluid. Cap portion 720 is adapted to have a length of flexible tubing 73 mounted thereto to communicate fluid from fluid reservoir 710A to the dilating catheter assembly as shown in FIG. 2.

In a preferred embodiment of this invention a rim 711 is formed on housing 71 and a second flexible diaphragm 713 is snapped over rim 711. Diaphragm 713 has a thin wall end portion 714 and a thicker wall edge portion 715 with an interior extending lip 716 adapted to snap over the rim 711 formed on housing 71. Mounting cap 72 includes bayonet threads 72A which cooperate with ears 619 formed on the walls of mounting cup 616 to provide a bayonet screw connect-disconnect mounting arrangement for the secondary fluid pump assembly 70 on primary pump chamber 61B. An annular portion 72B on cap 72 mates with a shoulder 712 formed on plastic housing 71 to urge rim 711 against the edge of the front wall 714 on diaphragm 713 to insure a fluid-tight seal between plastic housing 71 and diaphragm 713.

A resealing fluid entry port arrangement 74 is provided on plastic housing 71. This resealing fluid entry port arrangement comprises a cylindrical well 74A formed adjacent one wall of the plastic housing 71 between cap portion 720 and rim 711. A bottom wall 74B of well 74A is made thick enough to resist piercing by the point 81A of a syringe needle 81. Preferably a filling gate 74G is cemented to partly fill a channel formed in an interior wall of well 74A leaving a fluid fill opening 74G communicating between the interior of well 74A and the fluid reservoir interior 710A within housing 71. This filling gate, together with the tapered walls of well 74A, ensure that all air in the well will be pushed out ahead of fluid entering the well.

An aperture 74C forming the opening of well 74A is adapted to receive a resealing rubber membrane 74D preferably formed in the tapered configuration shown from a core-resistant rubber. A cap 74E having a top aperture 74F is cemented or ultrasonically welded over the open mouth 74C of well 74A to retain rubber membrane 74D in position. Cap 74E is formed to a slightly smaller inner diameter than the outer diameter of membrane 74D to produce a compression on membrane 74D which assists in resealing it against air leakage when vacuum is later drawn. Aperture 74F is adapted to admit the syringe needle 81 therethrough so that it can pierce the rubber membrane 74D and enter the well 74A.

As shown in FIG. 7 an end wall portion 620 of mounting cup 616 extends beyond the thin end wall 621 of diaphragm 61C to enable the mounting cup to at least partly receive diaphragm 713. Slots on apertures 618 are provided at spaced locations on end wall portions 620 to assist in letting air escape from between the two membranes as they are brought into contact.

FIGS. 8A and 8B illustrate a preferred method of filling the hydraulic cylinder 62 and primary pump chamber 61 with a relatively incompressible working fluid. For filling cylinder 62 and chamber 61, the actuator bar 51 shown in FIG. 3 is placed in the factory gun fill position with the pin 53 inserted in the detent aperture 51E in actuator bar 51. As shown in FIG. 8A, a solid disk 75 which may be made of plastic or metal is mounted over the first flexible diaphragm 61C in order to maintain the diaphragm in a generally flat condition while the cylinder and the primary fluid pump chamber are being evacuated and then filled with working fluid. Since the technique for filling the primary fluid pump assembly involves evacuating the air from the cylinder and primary pump chamber, the flat disk 75 prevents air at atmospheric pressure from collapsing the flexible end wall 621 of membrane 61C. As shown in FIG. 8B, the setup for filling the primary fluid pump assembly utilizes a filling system 90 which includes a bottle 91 serving as a reservoir for the fluid 92 to be introduced into the pump assembly. Bottle 91 has a stopper 96 sealing the top thereof. Tubing 93 is attached to the fill valve 62B on hydraulic cylinder 62. Tubing 93 is coupled by way of a tubing coupler 94 to a second section of tubing 95 extending through stopper 96 into the liquid reservoir 92. Another section of tubing 97 extends through the stopper into the space above the reservoir of liquid 92 and is connected to a two-way valve 98. Two-way valve 98 is manually settable to couple tubing section 97 to tubing section 101 leading to vacuum pump 100 or to couple tubing section 97 to a needle valve 99 which is vented to the atmosphere.

After the actuator bar of the inflation gun is set in the factory fill position so that the piston in cylinder 62 is in an intermediate location between its most rearward and forward positions, and after the block 75 has been mounted over diaphragm 61C, fill valve 62B is opened and two-way valve 98 is set to connect the tubing section 97 to tubing 101 leading to vacuum pump 100. Vacuum pump 100 is operated to evacuate the space above liquid 92 in bottle 91 which in turn evacuates air from the primary fluid pump assembly via the tubing sections 93 and 95. After evacuating the air from the primary fluid pump assembly, the two-way valve 98 is turned until the tubing section 97 communicates with the needle valve 99. As the space 91 above liquid reservoir 92 returns to atmospheric pressure, the pressure differential between it and the evacuated pump assembly pulls liquid from reservoir 92 into the fluid pump assembly filling it completely with very little trapped air. Thereafter the fill valve 62B is closed and the inflation gun is ready for operation.

The preferred material for filling the primary fluid pump assembly is a silicon oil which has a water-like viscosity. This material is preferred since it does not degas substantially under vacuum. Other fluids which have generally the same properties could also be utilized to fill the primary fluid pump assembly.

After the inflation gun has been filled, it may be sterilized before bringing into the operating room to be utilized in conjunction with a percutaneous transluminal coronary angioplasty procedure. The first step in preparing for the performance of this procedure utilizing the catheter inflation system of this invention is to remove the mounting cap 72 and the solid disk 75. Thereafter the actuator bar 51 is depressed until the latch channel 51A is in registration with the latch bar head 51H. Latch bar 51G is then pushed up to its top detent position to maintain the actuator bar 51 in the catheter fill position. In this catheter fill position, the flexible end wall 621 of flexible membrane 61C has a slightly concave shape labeled I in FIG. 7. The secondary fluid pump assembly 70 is then mounted to the primary pump chamber 61. As the flexible end wall 714 of the membrane 713 in secondary fluid pump assembly 70 comes into contact with the end wall 621 of membrane 61C, the air in the pocket between the two flexible membrane walls is gradually displaced and exits through the slots 618 in the side walls of the mounting cup 616. Thereafter the cap 72 is placed over the molded plastic housing 71 and the two assemblies are fastened together using the bayonet screw arrangement. When cap 72 is tightened down, the two flexible end walls 621 and 714 are in intimate contact with each other with little or no air between them.

The next step is to connect the tubing connector 44 onto the fitting on side arm 43 as shown in FIG. 2. To fill the dilating catheter assembly, both the catheter and the inflation gun may be rested on a table with the inflation gun laying on its side. As shown in FIG. 4, the inflation gun is adapted to lay on its back side with the flexible membrane 621 facing upward. A syringe 80 filled with radiocontrast fluid and having a sharp needle 81 thereon is utilized to fill the secondary fluid pump assembly 70. Needle 81 is pushed through the resealing element 74D shown in FIG. 7 into the well 74A. The bottom 74B of well 74A prevents the sharp point 81A of needle 81 from penetrating the bottom of the well and perforating either of the flexible diaphragm end walls underneath the well. Once the needle has been inserted the handle on syringe 80 may be operated to push radiocontrast fluid into the reservoir 710A. First the well 74A fills with the fluid, pushing air ahead of it, and then the fluid begins to spill over through the fill aperture 74H into the chamber 710A. After the chamber 710A is filled, the liquid passes through the channel 721 and the tube 73 into the connector 40 of the dilating catheter assembly. The liquid then passes through the connector into the passageway between the inner tube 14 and outer tube 15 of the catheter assembly. As the liquid enters the catheter assembly the air previously therein is flushed through a flush wire 24 which is extended through side arm 42 into the distensible balloon section 16. Preferably the connector assembly 40 is transparent so that the displacement of all air in the connector 40 and the catheter 10 can be visually observed during the fill operation. Once the catheter is completely filled with the radio contrast fluid the flush wire 24 is removed and the O-ring valve arrangement 46 is closed to preclude reentry of air or leakage of fluid from the system. In the filling process the balloon section 16 of the catheter has been at least partially inflated with the fluid.

After filling the catheter, the syringe 80 is removed and the resealing rubber membrane 74D closes back to form a fluid tight seal. Then, to deflate the balloon section 16 of the catheter, the actuator bar assembly 50 may be pushed in slightly. As the actuator bar is pushed in the sloped back wall of the channel 51A in the bottom thereof pushes the latch bar 51G downward out of the top detent position. Release of the actuator handle 50 then causes the handle to return to its most rearward position due to the spring bias thereon. As the handle assumes its greatest rearward position, a vacuum is pulled by the cylinder 62 in the primary fluid pump assembly which causes the two flexible end walls of the diaphragms to collapse and assume the position labeled III in FIG. 7. This produces a balloon-deflating vacuum in the secondary fluid pump assembly and the dilating catheter. This balloon-deflating vacuum condition is maintained by the inflation gun without the gun being held by a person. Consequently, insertion of the dilating catheter can be accomplished with the inflation gun itself maintaining the balloon-deflating vacuum in the dilating catheter.

After the dilating catheter has been inserted through the guiding catheter into the desired location wherein an atherosclerotic plaque restriction has occurred in the coronary artery, the balloon 16 on the catheter will be inflated by pushes in the actuator bar 51, causing the two flexible membrane walls 621 and 714 to be pushed into the shape labelled II in FIG. 7. This produces balloon-inflating pressure in the secondary fluid pump assembly and the dilating catheter assembly. The magnitude of balloon-inflating pressure is controlled by the setting of the pressure regulating valve using the setting thumb screw 63A extending out of the cap 58 on housing 55. The compound pressure gage 64 permits the operating room physician to monitor both the magnitude of the balloon-deflating vacuum and the magnitude of the balloon-inflating pressure.

From the above description many advantages of the catheter inflation system of this invention over the prior art system will be apparent. The system of this invention makes the dilating catheter assembly much easier to fill. The inflation gun produces and holds a balloon-deflating vacuum during catheter insertion without requiring a second person to maintain control over the production of that vacuum as in the prior art system using a syringe pump. The radiocontrast fluid placed in the secondary fluid pump assembly does not come in contact with the closed primary fluid pump assembly and thus has no corrosive effect on any of the parts of the inflation gun.

The secondary fluid pump assembly may be made a sterilizable, disposable component of the system, that is to say the dilating catheter assembly and the secondary fluid pump assembly may be detached from the inflation gun after the procedure has been performed and then disposed of. Since the inflation gun is not subjected to the radiocontrast fluid, it does not require cleaning after use but is available for immediate resterilization and reuse on another patient in another procedure. Since the secondary fluid pump assembly in the preferred embodiment is a closed fluid-tight assembly, the mess associated with disconnecting the pump assembly from the dilating catheter assembly in the prior art system is eliminated. Finally, the speed of the inflating and deflating action of the balloon in the dilating catheter is improved over that in the prior art system because leakage of air into the system is eliminated and consequently a more rapid communication of the pressure wave to the balloon section is provided. This increases the effectiveness of the procedure in compressing the material creating the atherosclerotic lesion.

While the catheter inflation system of this invention has been described above in connection with a preferred embodiment, it should be understood that numerous alternative implementations of various aspects of the system could be realized without departing from the basic concept of the invention. For example, referring back to FIG. 7, it would be possible to achieve the major advantages of this invention in an alternative embodiment which eliminates the second flexible membrane 713 associated with the secondary fluid pump assembly. In this alternative embodiment, the molded plastic housing 71 would be provided with a slightly larger diameter rim portion 711, i.e., a rim portion having a diameter matching that of the flexible diaphragm 61C. A slightly longer lip could be provided on the bottom of the rim to mate with the edge of the diaphragm 61C, with a fluid tight seal being provided by pressure being applied between the lip portion and the diaphragm 61C as the cap 72 is mounted to the mounting cup 616. Using this alternative approach, care would have to be taken when disassembling the secondary fluid pump assembly from the inflation gun after the procedure has been performed. Otherwise the radiocontrast fluid will spill out of the fluid reservoir section 710A as the disconnection is made. However, carefully unscrewing the cap 72 with the cap end 720 of the molded plastic housing 71 facing downward would retain all of the radiocontrast fluid in the reservoir 710A after disassembly. The fluid could then be dumped into a container and residual fluid on the membrane 621 could be wiped away.

It should be apparent that numerous configurations for the inflation gun and the various elements of the primary fluid pump assembly could be implemented. The overall arrangement of these elements shown in FIG. 3 is preferred due to the compactness of the design.

It will also be appreciated that numerous alternative approaches to providing the manual actuating means for driving the piston of the hydraulic cylinder could be implemented. Various alternative forms of the trigger mechanisms mounted on the pistol grip handle could be utilized.

FIG. 9 shows in schematic block diagram form an alternative remote pressure readout arrangement which could replace the mechanical dial pressure gage 64. An electronic pressure transducer 110 is coupled into the primary pump chamber 61, i.e., into the multiport block 61A shown in FIG. 6 in place of the dial gage 64. The analog output signal on line 111 from pressure transducer 110 is supplied to an analog to digital converter 115 which converts the analog signal to a digital word. This digital word could be supplied cover a cable 116 to a display driver 120 whose output would drive a liquid crystal display 125 by way of a drive signal cable 121. The liquid crystal display 125 could be adapted to mount on the bottom of the fluoroscope screen 130 which is utilized to visualize the position of the catheter within the patient. Utilizing this remote pressure readout the doctor could watch the pressure and adjust the maximum pressure desired while viewing the action of the balloon inflation and deflation on the fluoroscope screen. Various other electronic remote pressure readout systems of analog or digital type could also be implemented.

FIG. 10 shows an alternative approach involving automation of the driving of the piston in the hydraulic cylinder 62. The system shown in FIG. 10 utilizes an air cylinder 140 whose piston rod 141 is coupled by way of a piston rod coupler 135 to the piston rod 62D of hydraulic cylinder 62. Air cylinder 140 is a double-action cylinder having a retract air port 142 and an extend air port 143. When air under pressure is applied to the retract port 142, the piston in air cylinder retracts, carrying with it the piston 62D in hydraulic cylinder 62 to produce balloon-deflating vacuum. When compressed air is supplied to the extend port 143, the piston rod 141 of air cylinder 140 extends and drives the piston rod 62D forward to produce balloon-inflating pressure. Air valve 150 controls the supply of air under pressure from air compressor 160 (or compressed gas source) through air line 161 into the extend port or the retract port. Air valve 150 may be a two-position valve whose position is established by the operation of an internal solenoid which is, in turn, controlled by electrical signals supplied over control line 171 from a control panel switch arrangement 170. The exhaust ports 151 and 152 on air valve 150 alternately exhaust air from the air cylinder exiting one of the extend or retract ports as compressed air is supplied to the other port.

Other electro-mechanical arrangements for automating the drive means 50 for the hydraulic cylinder 62 could also be implemented. For example, piston rod 62D could be driven by an eccentric cam arrangement caused to rotate by an electric motor.

It should also be appreciated that instead of using a pressure regulating valve 63 in the primary fluid pump assembly, the hydraulic cylinder 62 could be coupled directly to the primary pump chamber 61. Control over the maximum pressure to be applied to the fluid in the primary pump chamber could then be provided, if desired, by a manually positionable actuator bar stop arrangement mounted in the pistol grip handle 59 or the actuator bar to limit the travel of the actuator bar 51. The pressure gage 64 could be utilized to determine the positioning of the stop means to calibrate its position to a particular desired maximum pressure for the inflation gun each time the gun is to be operated.

It will also be appreciated that numerous different approaches to mounting the secondary fluid pump assembly on the primary pump chamber could be implemented. Instead of the bayonet screw arrangement a complementary external thread on the mounting cup 616 could be provided in conjunction with internal threads formed on the cap 72. In addition, numerous different forms of clamp type mounting arrangements could be provided for accomplishing this mounting function.

The scope of this invention is accordingly not limited to the various preferred and alternate embodiments disclosed and discussed above since numerous modifications could be made without departing from the scope of the invention as claimed in the following claims.

What is claimed is:

1. In apparatus for the rapid inflation and deflation of a balloon-type dilating catheter assembly, a pistol grip housing adapted to be held in one hand and having spring loading actuator means mounted thereon adapted to be operated by a portion of said hand holding said housing between a released, balloon deflated position and an actuated balloon inflated position; pump means at least partly carried by said housing coupled to said actuator means to be actuated thereby, said pump means including a pump chamber adapted to be connected to said catheter assembly and piston means coupled to said actuator means for altering the fluid holding volume of said pump chamber; latching means carried on said housing for holding said actuating means in a catheter fill position intermediate said released, balloon deflation position and an actuated, balloon inflation position; and fill port means carried on said pump chamber for filling said pump chamber and said catheter assembly with a relatively incompressible fluid when said actuator means is latched in said catheter fill position, whereby a balloon deflating vacuum is automatically produced in said pump chamber when said actuator means is in said released position and a balloon inflating pressure is produced in said pump chamber when said actuator is operated to an actuated, balloon inflation position.

2. Apparatus as claimed in claim 1, wherein said pump chamber is a secondary pump chamber and said pump means further includes a primary pump chamber and a flexible diaphragm mounted between said primary and secondary pump chambers, said piston means being carried in said primary pump chamber and said flexible diaphragm forming a portion of one wall of said primary pump chamber to provide a completely sealed unit, said secondary pump chamber being adapted to mount to said primary pump chamber in a sealed relation to said flexible diaphragm, said primary pump chamber being filled with a relatively incompressible fluid while said diaphragm means is held in a substantially flat position and said actuating means is in a factory fill position intermediate said catheter fill position and said released position.

3. In apparatus for the rapid inflation and deflation of a balloon-type dilating catheter assembly,
  a primary fluid pump assembly comprising a primary pump chamber having a first flexible diaphragm forming one wall thereof, and a hydraulic cylinder including a piston for supplying fluid under pressure to said pump chamber, said pump assembly being filled with a relatively incompressible liquid while said piston is held in an intermediate fill position and said diaphragm is held substantially flat to produce both concave and convex shapes of said diaphragm as said piston is thereafter moved between forward and rearward positions;
  a secondary fluid pump assembly adapted to mount to said primary pump chamber and comprising a secondary pump chamber having a second flexible diaphragm forming one wall thereof and adapted to mate with said first flexible diaphragm, a resealing fluid entry port means for admitting fluid to said secondary chamber, means for mounting said secondary pump chamber to said primary pump chamber with said first and second diaphragms in intimate physical contact, and means for communicating fluid between said secondary pump chamber and said dilating catheter assembly; and
  means for driving said piston of said hydraulic cylinder between said forward and backward positions thereby to alternately create balloon-inflating pressure and balloon-deflating vacuum in said secondary pump chamber and said dilating catheter assembly when filled with a relatively incompressible fluid.

4. Apparatus as claimed in claim 3, wherein said primary fluid pump assembly is mounted in a portable housing including a pistol grip handle on one end, said hydraulic cylinder includes a piston rod extending into said handle, and said driving means comprises a pump actuator fastened to said piston rod, means mounting said actuator on said handle for enabling said actuator to drive said piston rod in response to manual operation by a hand holding said handle, and spring biasing means for biasing said actuator and said piston toward said rearward position.

5. Apparatus as claimed in claim 4, wherein said driving means further comprises means for releasably latching said actuator in an intermediate catheter fill position in which said first flexible working diaphragm in said primary pump chamber is slightly concave.

6. Apparatus as claimed in claim 5, wherein said pistol grip handle has a channel formed in the top rear portion thereof communicating with the rear wall of the handle, said piston rod of said hydraulic cylinder extends through said channel, said pump actuator comprises an actuator bar reciprocatingly mounted in said channel and fastened to said piston rod, said spring means includes at least a pair of compression springs mounted within said channel between an end wall thereof and said actuator bar for urging said actuator bar towards a backward position, and said latching means includes a latch channel formed in the bottom wall of said actuator bar and a latch bar and detent assembly mounted in said pistol grip handle, said latch bar having a latch head adapted to be pushed into said latch channel in said actuator bar for retaining said actuator bar in said catheter fill position.

7. Apparatus as claimed in claim 3, wherein said primary fluid pump assembly further comprises a compound pressure gage means communicating with said primary pump chamber for providing a readout of both positive and negative pressures relative to atmospheric pressure.

8. Apparatus as claimed in claim 3, wherein said secondary pump chamber comprises a molded plastic housing having a generally hollow, cylindrical configuration, one end of said housing being open and having a rim portion formed thereon, the other end of said housing having a cap portion formed thereon with a fluid channel extending therethrough and being fastened to a length of flexible plastic tubing to communicate fluid to said catheter assembly, said second flexible diaphragm having a generally cup-shaped configuration and being adapted to snap over said rim portion on said housing to form therewith a generally fluid tight seal.

9. Apparatus as claimed in claim 8, wherein said resealing fluid entry port comprises a well formed in one wall of said housing between said cap portion and said rim and adapted to receive the end of a syringe needle, a resealing rubber membrane fitted over the mouth of said well and adapted to be pierced by said needle, and a cap fastened to said housing over said rubber membrane and having an aperture in the top thereof adapted to admit said syringe needle into said well through said membrane, an interior wall of said well having a fill opening formed in a section thereof opposite the tip of said needle when inserted to communicate fluid from said well to the interior of said housing.

10. Apparatus as claimed in claim 8, wherein said primary pump chamber comprises a housing having a cylindrical open end with a rim formed thereon, said first flexible diaphragm having a generally cup-shaped configuration and being adapted to snap over said rim on said housing with a lip on said diaphragm extending behind said rim, and a mounting cup adapted to receive said housing and said first diaphragm including means fastening said housing to said cup, the walls of said mounting cup having a front portion extending beyond the end wall of said diaphragm and adapted to receive at least an end portion of said second diaphragm, said plastic housing having an annular external shoulder formed thereon parallel to and spaced from said rim, and said means for mounting said secondary pump chamber to said primary pump chamber comprises a mounting cap adapted to fit over said plastic housing and said mounting cup, said mounting cup engaging said shoulder on said plastic housing, and said mounting cap and said mounting cup having formed thereon cooperative threads of a bayonet mounting screw arrangement for fastening said mounting cap on said mounting cup while urging the end wall of said second diaphragm into contact with the end wall of said first diaphragm.

11. A sterilizable and disposable secondary fluid pumping assembly adapted to be releasably mated on one end to a balloon-type dilating catheter assembly and to be releasably coupled on another end to a primary fluid pump assembly which includes a primary pump chamber having a first flexible diaphragm forming one wall thereof, said assembly comprising a secondary pump chamber having a second flexible diaphragm forming one wall thereof and adapted to mate with said first flexible diaphragm, a resealing fluid entry port means for admitting fluid to said secondary chamber, means for mounting said secondary pump chamber to said primary pump chamber with said first and second diaphragms in intimate physical contact, and means for communicating fluid between said secondary pump chamber and said dilating catheter assembly.

12. Apparatus as claimed in claim 11, wherein said secondary pump chamber comprises a molded plastic housing having a generally hollow, cylindrical configuration, one end of said housing being open and having a rim portion formed thereon, the other end of said housing having a cap portion formed thereon with a fluid channel extending therethrough, said second flexible diaphragm having a generally cup-shaped configuration and being adapted to snap over said rim portion on said housing to form therewith a generally fluid tight seal; and said communicating means comprises a length of flexible plastic tubing fastened on one end to said cap portion of said plastic housing and having a fitting mounted on the other end thereof adapted to couple said tubing to said catheter assembly.

13. Apparatus as claimed in claim 12, wherein said resealing fluid entry port comprises a well formed in one wall of said plastic housing between said cap portion and said rim and adapted to receive the end of a syringe needle, a resealing rubber membrane fitted over the mouth of said well and adapted to be pierced by said needle and a cap fastened to said housing over said rubber membrane and having an aperture in the top thereof adapted to admit said syringe needle into said well through said membrane, an interior wall of said well having a fill opening formed in a section thereof opposite the top of said needle when inserted to communicate fluid from said well to the interior of said housing.

14. Apparatus as claimed in claim 3, wherein said primary fluid pump assembly further comprises a variable pressure regulating valve mounted between said hydraulic cylinder and said pump chamber to preset the maximum pressure of fluid supplied to said chamber by said cylinder.

15. Apparatus as claimed in claim 4, wherein said primary fluid pump assembly further comprises a compound pressure gage means communicating with said primary pump chamber for providing a readout of both positive and negative pressures relative to atmospheric pressure.

16. Apparatus as claimed in claim 15, wherein said compound pressure gage means is a mechanical pressure gage having a dial readout of both positive and negative pressures.

17. Apparatus as claimed in claim 15, wherein said compound pressure gage means comprises an electronic pressure transducer mounted on said primary pump chamber and electronic display means communicating with said pressure transducer means for providing a remote readout of pressure in said primary pump chamber.

18. Apparatus as claimed in claim 3, wherein said means for driving said piston comprises a double-acting fluid operated cylinder having a piston coupled to said piston of said hydraulic cylinder and extend and retract ports, means for delivering a supply of fluid under pressure for operating said double-acting cylinder, valving means for alternately coupling said fluid under pressure to said drive and retract ports of said fluid operated cylinder and switching means for operating said valve means.

19. In apparatus for the rapid inflation and deflation of a balloon type dilating catheter assembly,
a primary fluid pump assembly comprising a primary pump chamber having a first flexible diaphragm forming one wall thereof, and a hydraulic cylinder including a piston for supplying fluid under pressure to said pump chamber, said pump assembly being filled with a relatively incompressible liquid while said piston is held in an intermediate fill position and said diaphragm is held substantially flat to produce both concave and convex shapes of said diaphragm as said piston is thereafter moved between forward and rearward positions;
a secondary fluid pump assembly adapted to mount to said primary pump chamber and comprising a secondary pump chamber adapted to mate with said first flexible diaphragm in a fluid tight sealing relation, a resealing fluid entry port means for admitting fluid to said secondary chamber, means for mounting said secondary pump chamber to said primary pump chamber, and means for communicating fluid between said secondary pump chamber and said dilating catheter assembly; and
means for driving said piston of said hydraulic cylinder between said forward and backward positions thereby to alternately create balloon-inflating pressure and balloon-deflating vacuum in said secondary pump chamber and said dilating catheter assembly when filled with a relatively incompressible fluid.

20. A sterilizable and disposable secondary fluid pumping assembly adapted to be releasably mated on one end to a balloon-type dilating catheter assembly and to be releasably coupled on another and to a primary fluid pump assembly which includes a primary pump chamber having a first flexible diaphragm forming one wall thereof, said assembly comprising a secondary pump chamber adapted to mate with said first flexible diaphragm in a fluid tight sealing relation, a resealing fluid entry port means for admitting fluid to said secondary chamber, means for mounting said secondary pump chamber to said primary pump chamber in fluid tight sealing relation, and means for communicating fluid between said secondary pump chamber and said dilating catheter assembly.

21. Apparatus as claimed in claim 6, wherein said top of said pistol grip handle has a detent aperture formed therein communicating between the top surface and said channel, and said actuator bar has a detent aperture formed in a top surface thereof at a location adapted to register with said detent aperture in said housing when said actuator bar is partially pushed into said channel, said detent apertures being adapted to receive a latch pin when in registration with each other and being positioned to establish a factory fill position for said primary fluid pump assembly.

* * * * *